United States Patent [19]

Grimes

[11] 4,231,363
[45] Nov. 4, 1980

[54] GAS DELIVERY FACE SHIELD

[76] Inventor: Jerry L. Grimes, Star Rte., Box 517, Lytle Creek, Calif. 92358

[21] Appl. No.: 1,686

[22] Filed: Jan. 8, 1979

Related U.S. Application Data

[63] Continuation-in-part of Ser. No. 737,851, Nov. 1, 1976, abandoned.

[51] Int. Cl.³ ............................................. A61M 16/00
[52] U.S. Cl. ......................... 128/205.25; 128/206.28
[58] Field of Search ............... 128/185, 195, 196, 197, 128/201, 202, 205, 208, 140 R, 141 R, 142 R, 142.3, 142.4, 142.7, 146 R, 146.4, 146.7, 205.25, 206.28

[56] References Cited

U.S. PATENT DOCUMENTS

| | | | |
|---|---|---|---|
| 2,178,800 | 11/1939 | Lombard | 128/146 R |
| 2,617,415 | 11/1952 | Rosen et al. | 128/205 |
| 2,675,803 | 4/1954 | Kaslow | 128/205 |
| 2,764,152 | 9/1956 | Osterberg | 128/205 |
| 3,130,722 | 4/1964 | Dempsey et al. | 128/146 |
| 3,403,677 | 10/1968 | Struve | 128/205 |

*Primary Examiner*—Henry J. Recla
*Attorney, Agent, or Firm*—Seiler & Quirk

[57] ABSTRACT

A device for delivering gas to a patient comprises a unitary mask member for overlying the patient's nose and mouth and having an upper peripheral surface for lying in sealing engagement against the nose and cheeks, and a lower peripheral surface contiguous therewith disposed outwardly from the face, and a gas delivery member extending along the mask interior having orifices for delivering gas.

9 Claims, 7 Drawing Figures

GAS DELIVERY FACE SHIELD

REFERENCE TO OTHER APPLICATIONS

This application is a continuation-in-part of applicant's co-pending application Ser. No. 737,851 filed Nov. 1, 1976 now abandoned.

BACKGROUND OF THE INVENTION

Oxygen masks have been known and used for some time as efficient means for delivering oxygen to a patient during inhalation or respiratory therapy. More recently, these masks have been made of relatively soft and flexible plastic thereby making them disposable for single patient use. The modern and efficient masks have also been constructed so as to have a peripheral edge surface for fitting entirely around the patient's nose and cheeks, with the shorter masks passing beneath the patient's mouth along the chin and the longer masks extending under the patient's chin, but all in substantial sealing engagement so as to prevent loss of the oxygen containing gas delivered through the mask. Although such masks deliver the oxygen containing gas with desirable efficiency, since they are in substantial sealing engagement with the patient's face substantially entirely around the mask periphery, they offer some disadvantages. For example, the masks may become uncomfortable to the patient because of the extensive contact with the patient's face and also because of heat build up within the entirely enclosed mask area. In addition, $CO_2$ build up is often a problem in masks of this type which results in significant limitations of the upper end of oxygen delivery concentrations possible. Further because such a mask encloses the patient's lower face area, in order for the patient to speak or to take in food through the mouth, the mask must be removed or at least temporarily lifted which causes further discomfort and possible patient aggrevation or anxiety. Obviously during the time that the mask is removed, oxygen delivery to the patient is interrupted.

Of further concern is the possibility of a patient choking where fluids such as vomitus are aspirated from the enclosed mask area. Moreover, because the state of the art oxygen delivery masks require close fit about and around the patient's face in order to prevent leakage and achieve the intended and desired oxygen concentrations, the positioning of the mask and maintaining that position on the patient is quite important. If the mask becomes loosened or significantly moved, the sealing engagement of the mask edge with the patient's face will be disturbed thereby allowing undesirable venting of exterior ambient air into the mask as well as loss of oxygen and concomitant oxygen concentration change delivered to the patient, which may not be monitored. It is to the elimination and obviation of these disadvantages of state of the art masks that the device of the present invention is directed.

SUMMARY OF THE INVENTION

The gas delivering face shield device of the present invention offers a number of advantages over known oxygen delivery masks. For example, although the device is in sealing engagement around the patient's nose and cheeks so as to prevent oxygen from being directed upwardly into the patient's eyes resulting in discomfort or eye injury, the bottom of the shield around the patient's mouth is entirely open thereby preventing heat build up, presenting fewer pressure points or contact of the mask with the patient's facial skin, allowing the patient to talk more freely than an entirely enclosed mask, and also providing for the patient to take food or at least to be straw fed through the mouth without removing the shield or otherwise interrupting the desired oxygen delivery and concentrations. The device of the invention is relatively simple, comprising a unitary face shield in the preferred form of an arched shell and incorporating an oxygen delivery tube or pipe having a plurality of gas delivery orifices and which pipe is extended along the interior shield surface, preferably below the patient's nares. The features and characteristics of the device as well as additional advantages will be evident from the following detailed description.

DETAILED DESCRIPTION OF THE INVENTION

Figure 1:
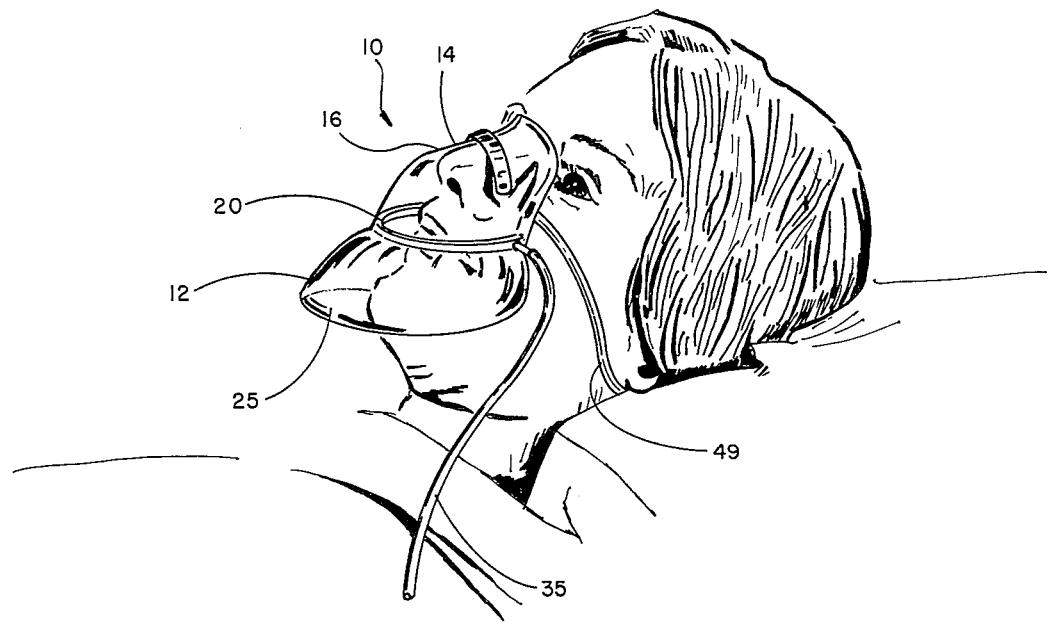
FIG. 1 is a perspective view of the oxygen delivering face shield of the invention showing it in place on a patient.

FIG. 1 illustrates the face shield 10 which comprises a unitary shield member 16 and a gas delivery member 20. As illustrated, the shield member is a shell, arached outwardly away from the patient's face and is divided into an upper portion 14 and lower portion 12 between which is located the gas delivery pipe 20. It should be appreciated that the shield member 16 is a unitary component, preferably molded of a single plastic sheet. However, in the preferred embodiment shown, the upper and lower shield portions are shaped somewhat differently and are separated by the gas delivery pipe.

Figure 2:
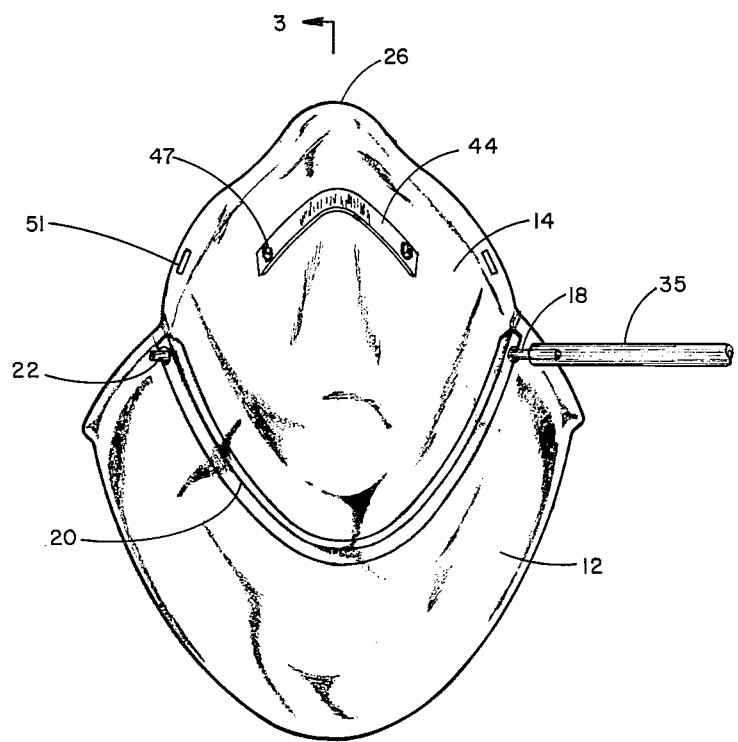
FIG. 2 is a front view of the face shield shown in FIG. 1.
Figure 3:
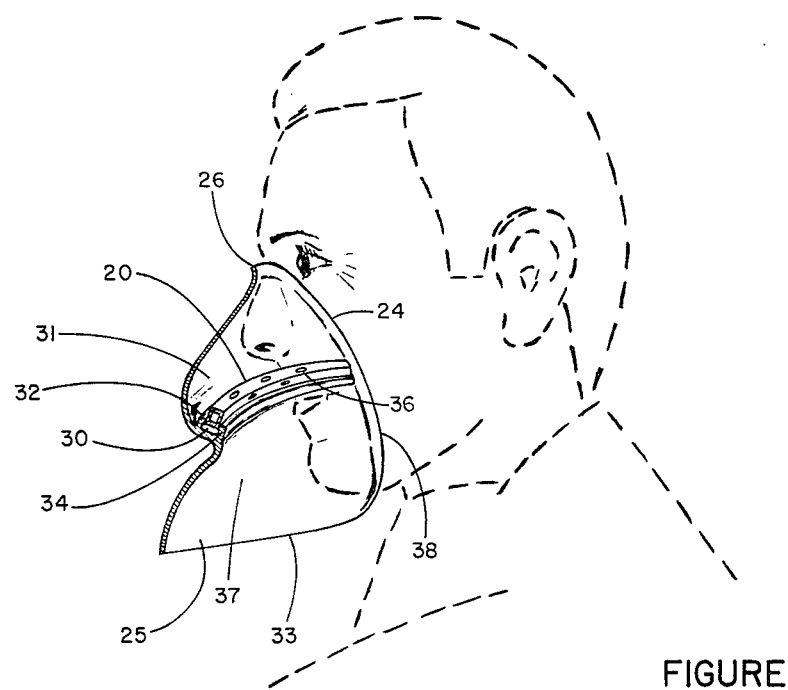
FIG. 3 is a sectional elevation of the face shield taken along lines 3—3 of FIG. 2.

FIGS. 2 and 3 illustrate the device in more detail, FIG. 2 illustrating the upper portion 14 having a peripheral edge surface which lies against the patient's face, particularly over the nose bridge and down the cheeks on both sides of the nose. The arched shell is formed between peripheral side edges and is bowed or arched away from the face and defines an interior cavity 31 into which gas from the delivery pipe is discharged for patient inhalation. The lower portion 12 forms a sort of shield or skirt which overlies the patient's mouth and chin and is outwardly from the patient's face so that there is no contact of this lower portion with the patient. Instead, as seen in FIGS. 1 and 3, the lower portion extends outwardly from the patient's mouth and chin area to also form an interior space or cavity 37. Such a space offers one of the specific and important advantages of the invention in allowing the patient to comfortably exhale and to speak and be easily heard without the mask entirely closing the nose and mouth area. Moreover, because the peripheral edge 33 of the lower portion is also arched or bowed away from the patient, an enlarged port or opening 25 is provided between the patient and the shield, which port communicates directly with the interior shield cavities. Accordingly, the inside of the device is open to the environment so that $CO_2$ and heat build up are minimized as well as allowing the patient to be fed at least through a straw without having to remove the mask or otherwise disturb the delivery of oxygen.

FIG. 3 also illustrates the preferred attachment of the oxygen gas delivery pipe 20. The pipe is preferably received in a channel 30 defined between a pair of ribs 32 and 34 extending arcuately along the interior shield surface. These ribs are integrally formed as part of the shield member and the gas delivery pipe is simply urged into the channel at the time of assembly. The ribs are preferably formed apart enough so that the pipe is forced therebetween with the ribs acting as support walls. Further, the ribs, channel and pipe are conveniently located between the upper and lower shell portions.

Figure 4:
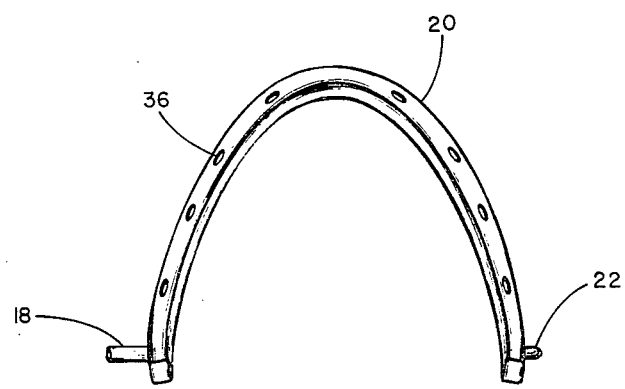
FIG. 4 is a top view of the gas delivery pipe utilized in the face shield.

The gas delivery pipe 20 is shown in more detail in FIG. 4. Preferably the pipe is molded from a more rigid material than that used to prepare the shield portion. One end of the gas delivery pipe is provided with a inlet member 18, having a length sufficient to adequately attach a gas supply tube 35. At the other pipe end is a button 22 or similar member for assisting in securing the pipe to the shield member. Accordingly, the shield member preferably has a pair of openings or holes, oppositely disposed and on each side, one for receiving the gas inlet member 18 and the other the button 22. Since the shield member is prepared from a softer, resilient and flexible plastic such as PVC or the like, button 22 may be oversized relative to the orifice through which it extends and have a groove or slot formed along the button so that the smaller orifice edges can fit into the slot once the button has been pushed through. This or any similar or equivalent means for securing the gas delivery pipe may be used. Again, channel 30 further assists in supporting and fixing the gas delivery pipe within the shield interior surface, with the pipe being pressed or otherwise urged between the two ribs forming and defining the channel. Although gas inlet member 18 is shown positioned at one end of pipe 20, it may be instead located anywhere along the pipe, for example, in the middle of the shield. In addition, the ends of the pipe may be inset somewhat from the side shield edges to avoid any patient discomfort. An alternative means for supplying oxygen to the pipe comprises using a gas inlet member at both ends of pipe 20, with a gas supply tube connected to each inlet member. Such supply tubes may be extended over the patient's ears to assist in keeping the shield in place on the patient, or may be drawn together under the patient's chin.

The gas delivery pipe is provided with a plurality of openings or orifices 36 through which oxygen containing gas is delivered within the shield for patient therapy. FIGS. 1 and 3 further illustrate the disposition of pipe 20 relative to the patient's nostrils and mouth. Since the pipe is arched or arcuate shaped to conform to the arched shield interior surface, it is disposed below or lower than the patient's nares throughout most of its length. Accordingly, it is preferred that the orifices 36 be positioned so as to direct oxygen containing gas toward the patient and at least somewhat upwardly toward the nares. Moreover, in a preferred embodiment, oxygen delivery pipe 20 is also provided with a plurality of gas delivery orifices 42 which direct a portion of the oxygen containing gas toward the patient's mouth or lower part of the shield. The purpose for such downwardly gas directing orifices is to insure that a sufficient supply of oxygen containing gas will be delivered to the patient even is the person is breathing from his or her mouth. For example, if the patient's nasal passageway is occluded or the patient is otherwise breathing from the mouth, with all of the oxygen containing gas being directed upwardly, the desired concentrations of oxygen may not be inhaled by the patient because the shield is open at the bottom. The specific number of orifices may be varied widely depending on orifice sizes used, oxygen flow rates, etc. Normally, it is more desirable to incorporate more upwardly directing orifices, preferably between about 4 and 20, with downwardly directing orifices numbering between about 2 and 8.

Figure 6:
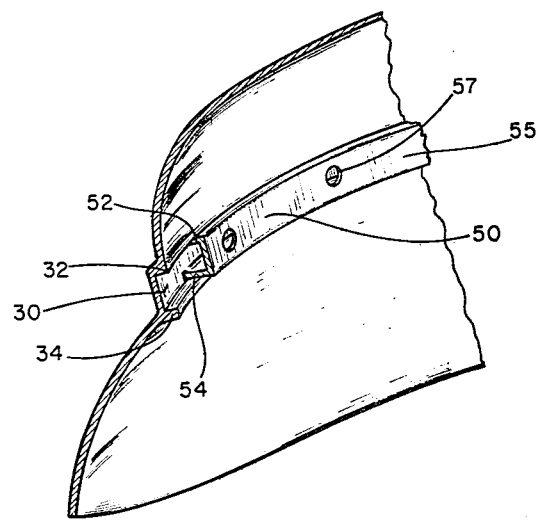
FIG. 6 is a partial sectional view of the face shield illustrating another embodiment of a gas delivery pipe.
Figure 7:
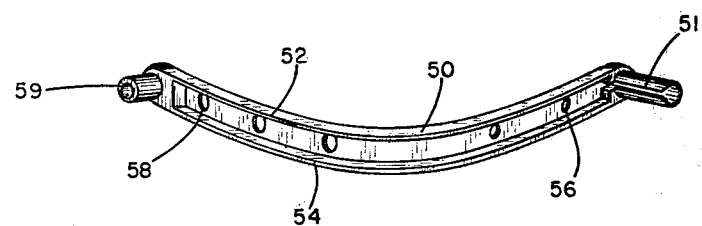
FIG. 7 is a view of the interior of the gas delivery pipe embodiment of FIG. 6.

FIGS. 6 and 7 illustrate another gas delivery pipe embodiment. The pipe consists of a passageway formed by channel 30 and conduit 50. The conduit has flanges 52 and 54 which engage ribs 32 and 34, respectively, to form the passageway along which oxygen is introduced for delivery to a patient. With the ribs relatively flexible and the flanges relatively stiff, the latter may fit snugly against the ribs to form a gas tight seal to prevent oxygen leakage along the passageway. Thus, the conduit acts as a cover sealingly engaging the ribs to form the passageway. Moreover, the conduit 50 is relatively easy to form or mold as compared to the gas delivery pipe of the previous embodiment. For assembly of the device, the conduit is simply fitted into the channel with button 59 and inlet pipe 51 inserted into openings on the side of the shield, in a manner as described for the previous embodiment.

The conduit preferably has a single major exposed outer surface 55 having a plurality of gas delivery ports 57. The surface may be curved or flat, and because of the upwardly slanted direction of ribs 32 and 34, when the conduit is fitted in place, surface 55 faces upwardly, toward the patient's mouth and nose, when the shield is in place on a patient as shown in FIG. 1. Because of the arcuate shape of the passageway, it extends to at least slightly below the patient's mouth at its lowest point, as also shown in FIG. 1. Thus, with major exposed surface 55 having ports 57 thereon facing toward the patient's mouth and nose, improved oxygen delivery to a patient, whether breathing through the mouth, nose, or both, is achieved.

FIG. 7 also shows an improved and preferred oxygen delivery port system. In this embodiment, the ports vary in size along the passageway, port 56, nearest gas inlet pipe 51 being smallest, and port 58, furthest from the pipe, being largest. The intermediate ports may be graduated in size the further they are away from the inlet pipe. It has also been found to be preferably to have fewer and smaller ports on the half of the conduit nearest the pipe. As shown, two smaller ports are on the side nearest the inlet pipe, and three large ports on the other side. Such a feature provides more even flow and distribution of oxygen out the the length of the passageway into the interior shield cavity.

FIG. 3 illustrates another important feature of the invention, specifically the gas sealing engagement of the shield member at the patient's nose and cheek area. The upper shield end 26 is arch shaped to comfortably overlie the patient's nose bridge. Optionally, and preferably, a flexible metal strip 44 is also secured to the exterior mask surface which can be easily bent to further assist the mask in forming to the general contour of a patient's face. The metal is preferably soft such as aluminum so that it can be easily bent and formed by hand once the shield is placed on the patient. Protuberances or tabs 47 are formed on each side of the shield for securing the metal strip 44 as shown in FIG. 2. The upper peripheral edge surface 24 is also formed to provide a gently rounded or curved surface where it is compressed against the patient's face to form the proper seal. Although an outward curved surface 26 is shown, i.e., where the outer edge is directed away from the shield interior or center opposite curve such as is used in some state of the art oxygen masks where the shield edge is cured inwardly. Either shape may be used, so long as sealing engagement is provided to prevent the oxygen containing gas directed upwardly in the shield from passing to the patient's eyes, which could cause undesirable drying or other eye injury or discomfort.

On the other hand, the lower portion of the shield need not be so formed since there is no engagement of the peripheral lower portion edge with the patient's face. Although inner edge 38 may lightly touch the patient's face in the lower part of the cheeks adjacent the mouth. The lower outwardly extending peripheral surface 33 does not make contact, and indeed, is designed to provide an opening as previously described. In any event, it is understood that there is no problem of any gas sealing engagement of the lower portion of the shield member, below the gas delivery tube, since it is intended and specifically provided that the lower mask portion be open as described. The face shield according to the invention provides delivered patient oxygen concentration of between 22 and 65% at flowrates between 1 and 10 liters per minute. Thus, accurate deliveries through the low and medium concentration ranges can be achieved. Moreover, because of the open bottom feature, there is no problem with $CO_2$ accumulation in the shield due to constant oxygen flow flushing exhaled gas into the atmosphere.

Figure 5:
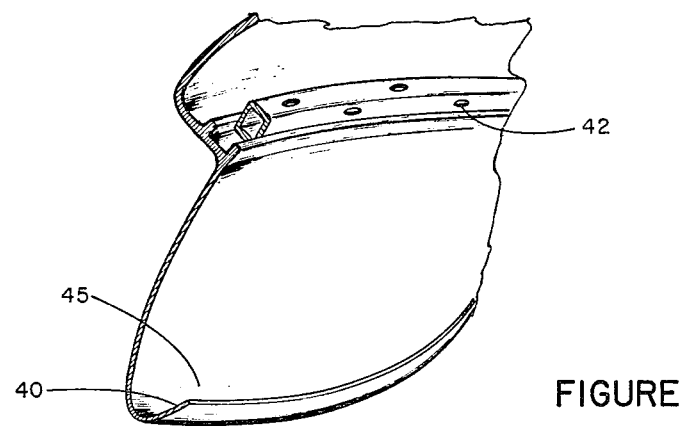
FIG. 5 is a partial sectional view illustrating another embodiment of the face shield and gas delivery orifices.

A further optional embodiment is an inwardly directing curl illustrated in FIG. 5 which provides or forms a sort of pocket 45 to assist in increasing oxygen concentration within the shield. In this embodiment, the bottom edge 40 of the lower shield portion is curved inward and slightly upward toward the shield interior to form the pocket 45, which feature has been found to increase oxygen concentration within the shield without otherwise increasing the concentration or volume of oxygen delivered.

As previously noted, the face shield is preferably made of a soft, resilient, and flexible material such as PVC (polyvinyl chloride) or other suitable and equivalent material. The gas delivery pipe is produced from a more rigid material such as rigid PVC or rigid polyethylene, polypropylene or the like. When these components are separately formed, they are assembled in a simple manner as previously described, utilizing the formed channel shown. Alternatively, it may be desirable to mold the device from a single mold in which the gas delivery pipe is integrally formed with the shield member. Accordingly, any method of preparing the shield member having the sealing engagement with the face along the upper portion, and the open lower portion and otherwise delivering oxygen through a plurality of orifices within the device, may be utilized.

Any suitable means for securing the shield to the patient's head such as an elastic band 49 secured through openings 51 as shown in FIGS. 1 and 2, or any other equivalent means may be used. It will be understood, because of the advantages of the invention, that the placement of the device is not so critical since a gas tight seal around the patient's lower face area is not required. Moreover, because of the open bottom feature, patient comfort is maximized as is drainage from the patient's mouth area without danger of aspiration of liquids. These as well as other advantages and modifications within the purview of the invention will be evident to those skilled in the art.

I claim:

1. A device for delivering oxygen to a patient during respiratory therapy comprising:
    a unitary, shape retaining shell member adapted to overlie a patient's nose and mouth,
    a gas delivery member extending across the shell member interior and dividing said shell member into an upper portion and a lower portion, said upper portion having a peripheral surface adapted to provide a substantially gas tight seal with the patient's nose bridge and cheeks, said lower portion having a lower edge spaced outwardly thereby providing a lower opening between said mask lower edge and the patient's face, said upper and lower portions being arched outwardly from said gas delivery member and thereby in relation to the patient's face and forming an enlarged upper and lower chamber, respectively, said gas delivery member having a plurality of orifices directed into said upper chamber for directing oxygen thereto, whereby oxygen delivered to said device through said gas delivery member results in substantially greater oxygen concentration in said upper chamber than in said lower chamber.

2. The device of claim 1 wherein the shell member is flexible.

3. The device of claim 1 wherein said lower edge is directed inwardly in relation to a patient.

4. The device of claim 1 wherein the gas delivery member is an elongated pipe having a plurality of gas delivery orifices therealong and having means for connecting a gas supply tube.

5. The device of claim 4 wherein said shell member includes a channel formed along the interior surface receiving the pipe.

6. The device of claim 5 wherein said pipe is arched downwardly toward said lower edge and wherein said gas delivery orifices direct said gas upwardly.

7. The device of claim 5 wherein said pipe is arched downwardly toward said lower edge and wherein a portion of said gas delivering orifices direct gas upwardly and a portion of said orifices direct gas downwardly toward said lower edge.

8. The device of claim 1 wherein said gas delivery member comprises a channel formed along the interior surface of said shell member, and a cover therefor sealingly engaging said channel to form a passageway therealong, said cover having a plurality of gas delivery ports therealong.

9. The device of claim 8 wherein said passageway is arched downwardly toward said lower edge.

* * * * *